(12) United States Patent
Hannula et al.

(10) Patent No.: US 8,452,364 B2
(45) Date of Patent: May 28, 2013

(54) SYSTEM AND METHOD FOR ATTACHING A SENSOR TO A PATIENT'S SKIN

(75) Inventors: Don L. Hannula, San Luis Obispo, CA (US); Paul D. Mannheimer, Danville, CA (US); Albert L. Ollerdessen, Danville, CA (US)

(73) Assignee: Covidien LLP, Mansfield, MA (US)

( * ) Notice: Subject to any disclaimer, the term of this patent is extended or adjusted under 35 U.S.C. 154(b) by 1176 days.

(21) Appl. No.: 12/343,783

(22) Filed: Dec. 24, 2008

(65) Prior Publication Data

US 2009/0171177 A1    Jul. 2, 2009

Related U.S. Application Data

(60) Provisional application No. 61/009,355, filed on Dec. 28, 2007.

(51) Int. Cl.
*A61B 5/00* (2006.01)
(52) U.S. Cl.
USPC ........................ 600/322; 600/323; 600/344
(58) Field of Classification Search
USPC ............... 600/322, 323, 329, 344, 391, 392, 600/500, 502
See application file for complete search history.

(56) References Cited

U.S. PATENT DOCUMENTS

| | | |
|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

(Continued)

*Primary Examiner* — Julian Woo
(74) *Attorney, Agent, or Firm* — Fletcher Yoder

(57) ABSTRACT

A method and apparatus for affixing a sensor adjacent a tissue site is disclosed. In an embodiment, the spectrophotometric sensor comprises, a sensor body, one or more light emitters, one or more photodetectors, and a light scattering medium capable of increasing at least one of the effective detection area of the one or more photodetectors or the effective emission area of the one or more light emitters.

31 Claims, 8 Drawing Sheets

U.S. PATENT DOCUMENTS

| | | | |
|---|---|---|---|
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |

| Patent No. | Date | Inventor |
|---|---|---|
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |

| Patent | Date | Inventor |
|---|---|---|
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddart et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |

| Patent | Type | Date | Inventor |
|---|---|---|---|
| 6,438,399 | B1 | 8/2002 | Kurth |
| 6,449,501 | B1 | 9/2002 | Reuss |
| 6,453,183 | B1 | 9/2002 | Walker |
| 6,453,184 | B1 | 9/2002 | Hyogo et al. |
| 6,456,862 | B2 | 9/2002 | Benni |
| 6,461,305 | B1 | 10/2002 | Schnall |
| 6,463,310 | B1 | 10/2002 | Swedlow et al. |
| 6,463,311 | B1 | 10/2002 | Diab |
| 6,466,808 | B1 | 10/2002 | Chin et al. |
| 6,466,809 | B1 | 10/2002 | Riley |
| 6,470,199 | B1 | 10/2002 | Kopotic et al. |
| 6,470,200 | B2 | 10/2002 | Walker et al. |
| 6,480,729 | B2 | 11/2002 | Stone |
| 6,490,466 | B1 | 12/2002 | Fein et al. |
| 6,496,711 | B1 | 12/2002 | Athan et al. |
| 6,498,942 | B1 | 12/2002 | Esenaliev et al. |
| 6,501,974 | B2 | 12/2002 | Huiku |
| 6,501,975 | B2 | 12/2002 | Diab et al. |
| 6,505,060 | B1 | 1/2003 | Norris |
| 6,505,061 | B2 | 1/2003 | Larson |
| 6,505,133 | B1 | 1/2003 | Hanna et al. |
| 6,510,329 | B2 | 1/2003 | Heckel |
| 6,510,331 | B1 | 1/2003 | Williams et al. |
| 6,512,937 | B2 | 1/2003 | Blank et al. |
| 6,515,273 | B2 | 2/2003 | Al-Ali |
| 6,519,484 | B1 | 2/2003 | Lovejoy et al. |
| 6,519,486 | B1 | 2/2003 | Edgar, Jr. et al. |
| 6,519,487 | B1 | 2/2003 | Parker |
| 6,525,386 | B1 | 2/2003 | Mills et al. |
| 6,526,300 | B1 | 2/2003 | Kiani et al. |
| 6,526,301 | B2 | 2/2003 | Larsen et al. |
| 6,541,756 | B2 | 4/2003 | Schulz et al. |
| 6,542,764 | B1 | 4/2003 | Al-Ali et al. |
| 6,546,267 | B1 | 4/2003 | Sugiura et al. |
| 6,553,241 | B2 | 4/2003 | Mannheimer et al. |
| 6,553,242 | B1 | 4/2003 | Sarussi |
| 6,553,243 | B2 | 4/2003 | Gurley |
| 6,556,852 | B1 | 4/2003 | Schulze et al. |
| 6,560,470 | B1 | 5/2003 | Pologe |
| 6,564,077 | B2 | 5/2003 | Mortara |
| 6,564,088 | B1 | 5/2003 | Soller et al. |
| 6,571,113 | B1 | 5/2003 | Fein et al. |
| 6,571,114 | B1 | 5/2003 | Koike et al. |
| 6,574,491 | B2 | 6/2003 | Elghazzawi |
| 6,580,086 | B1 | 6/2003 | Schulz et al. |
| 6,584,336 | B1 | 6/2003 | Ali et al. |
| 6,587,703 | B2 | 7/2003 | Cheng et al. |
| 6,587,704 | B1 | 7/2003 | Fine et al. |
| 6,589,172 | B2 | 7/2003 | Williams et al. |
| 6,591,122 | B2 | 7/2003 | Schmitt |
| 6,591,123 | B2 | 7/2003 | Fein et al. |
| 6,594,511 | B2 | 7/2003 | Stone et al. |
| 6,594,512 | B2 | 7/2003 | Huang |
| 6,594,513 | B1 | 7/2003 | Jobsis et al. |
| 6,597,931 | B1 | 7/2003 | Cheng et al. |
| 6,597,933 | B2 | 7/2003 | Kiani et al. |
| 6,600,940 | B1 | 7/2003 | Fein et al. |
| 6,606,510 | B2 | 8/2003 | Swedlow et al. |
| 6,606,511 | B1 | 8/2003 | Ali et al. |
| 6,606,512 | B2 | 8/2003 | Muz et al. |
| 6,615,064 | B1 | 9/2003 | Aldrich |
| 6,615,065 | B1 | 9/2003 | Barrett et al. |
| 6,618,602 | B2 | 9/2003 | Levin et al. |
| 6,622,034 | B1 | 9/2003 | Gorski et al. |
| 6,628,975 | B1 | 9/2003 | Fein et al. |
| 6,631,281 | B1 | 10/2003 | Kästle |
| 6,643,530 | B2 | 11/2003 | Diab et al. |
| 6,643,531 | B1 | 11/2003 | Katarow |
| 6,647,279 | B2 | 11/2003 | Pologe |
| 6,647,280 | B2 | 11/2003 | Bahr et al. |
| 6,650,917 | B2 | 11/2003 | Diab et al. |
| 6,650,918 | B2 | 11/2003 | Terry |
| 6,654,621 | B2 | 11/2003 | Palatnik et al. |
| 6,654,622 | B1 | 11/2003 | Eberhard et al. |
| 6,654,623 | B1 | 11/2003 | Kästle |
| 6,654,624 | B2 | 11/2003 | Diab et al. |
| 6,658,276 | B2 | 12/2003 | Kianl et al. |
| 6,658,277 | B2 | 12/2003 | Wassermann |
| 6,662,033 | B2 | 12/2003 | Casciani et al. |
| 6,665,551 | B1 | 12/2003 | Suzuki |
| 6,668,182 | B2 | 12/2003 | Hubelbank |
| 6,668,183 | B2 | 12/2003 | Hicks et al. |
| 6,671,526 | B1 | 12/2003 | Aoyagi et al. |
| 6,671,528 | B2 | 12/2003 | Steuer et al. |
| 6,671,530 | B2 | 12/2003 | Chung et al. |
| 6,671,531 | B2 | 12/2003 | Al-Ali et al. |
| 6,671,532 | B1 | 12/2003 | Fudge et al. |
| 6,675,031 | B1 | 1/2004 | Porges et al. |
| 6,678,543 | B2 | 1/2004 | Diab et al. |
| 6,681,126 | B2 | 1/2004 | Solenberger |
| 6,681,128 | B2 | 1/2004 | Steuer et al. |
| 6,681,454 | B2 | 1/2004 | Modgil et al. |
| 6,684,090 | B2 | 1/2004 | Ali et al. |
| 6,684,091 | B2 | 1/2004 | Parker |
| 6,694,160 | B2 | 2/2004 | Chin |
| 6,697,653 | B2 | 2/2004 | Hanna |
| 6,697,655 | B2 | 2/2004 | Sueppel et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,699,199 | B2 | 3/2004 | Asada et al. |
| 6,701,170 | B2 | 3/2004 | Stetson |
| 6,702,752 | B2 | 3/2004 | Dekker |
| 6,707,257 | B2 | 3/2004 | Norris |
| 6,708,049 | B1 | 3/2004 | Berson et al. |
| 6,709,402 | B2 | 3/2004 | Dekker |
| 6,711,424 | B1 | 3/2004 | Fine et al. |
| 6,711,425 | B1 | 3/2004 | Reuss |
| 6,714,803 | B1 | 3/2004 | Mortz |
| 6,714,804 | B2 | 3/2004 | Al-Ali et al. |
| 6,714,805 | B2 | 3/2004 | Jeon et al. |
| RE38,492 | E | 4/2004 | Diab et al. |
| 6,719,686 | B2 | 4/2004 | Coakley et al. |
| 6,719,705 | B2 | 4/2004 | Mills |
| 6,720,734 | B2 | 4/2004 | Norris |
| 6,721,584 | B2 | 4/2004 | Baker, Jr. et al. |
| 6,721,585 | B1 | 4/2004 | Parker |
| 6,725,074 | B1 | 4/2004 | Kästle |
| 6,725,075 | B2 | 4/2004 | Al-Ali |
| 6,731,963 | B2 | 5/2004 | Finarov et al. |
| 6,731,967 | B1 | 5/2004 | Turcott |
| 6,735,459 | B2 | 5/2004 | Parker |
| 6,745,060 | B2 | 6/2004 | Diab et al. |
| 6,745,061 | B1 | 6/2004 | Hicks et al. |
| 6,748,253 | B2 | 6/2004 | Norris et al. |
| 6,748,254 | B2 | 6/2004 | O'Neill et al. |
| 6,754,515 | B1 | 6/2004 | Pologe |
| 6,754,516 | B2 | 6/2004 | Mannheimer |
| 6,760,607 | B2 | 7/2004 | Al-All |
| 6,760,609 | B2 | 7/2004 | Jacques |
| 6,760,610 | B2 | 7/2004 | Tscupp et al. |
| 6,763,255 | B2 | 7/2004 | DeLonzor et al. |
| 6,763,256 | B2 | 7/2004 | Kimball et al. |
| 6,770,028 | B1 | 8/2004 | Ali et al. |
| 6,771,994 | B2 | 8/2004 | Kiani et al. |
| 6,773,397 | B2 | 8/2004 | Kelly |
| 6,778,923 | B2 | 8/2004 | Norris et al. |
| 6,780,158 | B2 | 8/2004 | Yarita |
| 6,792,300 | B1 | 9/2004 | Diab et al. |
| 6,793,654 | B2 | 9/2004 | Lemberg |
| 6,801,797 | B2 | 10/2004 | Mannheimer et al. |
| 6,801,798 | B2 | 10/2004 | Geddes et al. |
| 6,801,799 | B2 | 10/2004 | Mendelson |
| 6,801,802 | B2 | 10/2004 | Sitzman et al. |
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,811,538 | B2 | 11/2004 | Westbrook et al. |
| 6,813,511 | B2 | 11/2004 | Diab et al. |
| 6,816,741 | B2 | 11/2004 | Diab |
| 6,819,950 | B2 | 11/2004 | Mills |
| 6,822,564 | B2 | 11/2004 | Al-Ali |
| 6,825,619 | B2 | 11/2004 | Norris |
| 6,826,419 | B2 | 11/2004 | Diab et al. |
| 6,829,496 | B2 | 12/2004 | Nagai et al. |
| 6,830,711 | B2 | 12/2004 | Mills et al. |
| 6,836,679 | B2 | 12/2004 | Baker, Jr. et al. |

| | | | | | | |
|---|---|---|---|---|---|---|
| 6,839,579 B1 | 1/2005 | Chin | 7,236,811 B2 | 6/2007 | Schmitt | |
| 6,839,580 B2 | 1/2005 | Zonios et al. | 7,248,910 B2 | 7/2007 | Li et al. | |
| 6,839,582 B2 | 1/2005 | Heckel | 7,254,433 B2 | 8/2007 | Diab et al. | |
| 6,839,659 B2 | 1/2005 | Tarassenko et al. | 7,254,434 B2 | 8/2007 | Schulz et al. | |
| 6,842,635 B1 | 1/2005 | Parker | 7,257,438 B2 | 8/2007 | Kinast | |
| 6,845,256 B2 | 1/2005 | Chin et al. | 7,263,395 B2 | 8/2007 | Chan et al. | |
| 6,850,787 B2 | 2/2005 | Weber et al. | 7,272,426 B2 | 9/2007 | Schmid | |
| 6,850,788 B2 | 2/2005 | Al-Ali | 7,280,858 B2 | 10/2007 | Al-Ali et al. | |
| 6,850,789 B2 | 2/2005 | Schweitzer, Jr. et al. | 7,295,866 B2 | 11/2007 | Al-Ali et al. | |
| 6,861,639 B2 | 3/2005 | Al-Ali | 7,297,119 B2 | 11/2007 | Westbrook et al. | |
| 6,863,652 B2 | 3/2005 | Huang et al. | 7,305,262 B2 | 12/2007 | Brodnick et al. | |
| 6,865,407 B2 | 3/2005 | Kimball et al. | 7,313,427 B2 | 12/2007 | Benni | |
| 6,879,850 B2 | 4/2005 | Kimball | 7,315,753 B2 | 1/2008 | Baker, Jr. et al. | |
| 6,882,874 B2 | 4/2005 | Huiku | 8,190,229 B2 * | 5/2012 | Lowery et al. | 600/323 |
| 6,889,153 B2 | 5/2005 | Dietiker | 2001/0021803 A1 | 9/2001 | Blank et al. | |
| 6,898,452 B2 | 5/2005 | Al-Ali et al. | 2001/0051767 A1 | 12/2001 | Williams et al. | |
| 6,909,912 B2 | 6/2005 | Melker | 2002/0026109 A1 | 2/2002 | Diab et al. | |
| 6,912,413 B2 | 6/2005 | Rantala et al. | 2002/0028990 A1 | 3/2002 | Shepherd et al. | |
| 6,916,289 B2 | 7/2005 | Schnall | 2002/0038078 A1 | 3/2002 | Ito | |
| 6,920,345 B2 | 7/2005 | Al-Ali et al. | 2002/0042558 A1 | 4/2002 | Mendelson | |
| 6,931,269 B2 | 8/2005 | Terry | 2002/0068859 A1 | 6/2002 | Knopp | |
| 6,934,570 B2 | 8/2005 | Kiani et al. | 2002/0103423 A1 | 8/2002 | Chin et al. | |
| 6,939,307 B1 | 9/2005 | Dunlop | 2002/0128544 A1 | 9/2002 | Diab et al. | |
| 6,941,162 B2 | 9/2005 | Fudge et al. | 2002/0133067 A1 | 9/2002 | Jackson, III | |
| 6,947,781 B2 | 9/2005 | Asada et al. | 2002/0156354 A1 | 10/2002 | Larson | |
| 6,950,687 B2 | 9/2005 | Al-Ali | 2002/0173706 A1 | 11/2002 | Takatani | |
| 6,963,767 B2 | 11/2005 | Rantala et al. | 2002/0173709 A1 | 11/2002 | Fine et al. | |
| 6,971,580 B2 | 12/2005 | DeLonzor et al. | 2002/0190863 A1 | 12/2002 | Lynn | |
| 6,983,178 B2 | 1/2006 | Fine et al. | 2002/0198442 A1 | 12/2002 | Rantala et al. | |
| 6,985,763 B2 | 1/2006 | Boas et al. | 2003/0018243 A1 | 1/2003 | Gerhardt et al. | |
| 6,985,764 B2 | 1/2006 | Mason et al. | 2003/0036690 A1 | 2/2003 | Geddes et al. | |
| 6,990,426 B2 | 1/2006 | Yoon et al. | 2003/0045785 A1 | 3/2003 | Diab et al. | |
| 6,992,751 B2 | 1/2006 | Al-Ali et al. | 2003/0073889 A1 | 4/2003 | Keilbach et al. | |
| 6,992,772 B2 | 1/2006 | Block et al. | 2003/0073890 A1 | 4/2003 | Hanna | |
| 6,993,371 B2 | 1/2006 | Kiani et al. | 2003/0100840 A1 | 5/2003 | Sugiura et al. | |
| 6,993,372 B2 | 1/2006 | Fine et al. | 2003/0132495 A1 | 7/2003 | Mills et al. | |
| 6,996,427 B2 | 2/2006 | Ali et al. | 2003/0135099 A1 | 7/2003 | Al-Ali | |
| 7,003,338 B2 | 2/2006 | Weber et al. | 2003/0162414 A1 | 8/2003 | Schulz et al. | |
| 7,003,339 B2 | 2/2006 | Diab et al. | 2003/0171662 A1 | 9/2003 | O'Connor et al. | |
| 7,006,855 B1 | 2/2006 | Sarussi | 2003/0176776 A1 | 9/2003 | Huiku | |
| 7,006,856 B2 | 2/2006 | Baker, Jr. et al. | 2003/0181799 A1 | 9/2003 | Lindekugel et al. | |
| 7,016,715 B2 | 3/2006 | Stetson | 2003/0187337 A1 | 10/2003 | Tarassenko et al. | |
| 7,020,507 B2 | 3/2006 | Scharf et al. | 2003/0195402 A1 | 10/2003 | Fein et al. | |
| 7,024,233 B2 | 4/2006 | Ali et al. | 2003/0197679 A1 | 10/2003 | Ali et al. | |
| 7,024,235 B2 | 4/2006 | Melker et al. | 2003/0212316 A1 | 11/2003 | Leiden et al. | |
| 7,025,728 B2 | 4/2006 | Ito et al. | 2003/0225323 A1 | 12/2003 | Kiani et al. | |
| 7,027,849 B2 | 4/2006 | Al-Ali et al. | 2003/0225337 A1 | 12/2003 | Scharf et al. | |
| 7,027,850 B2 | 4/2006 | Wasserman | 2003/0236452 A1 | 12/2003 | Melker et al. | |
| 7,035,697 B1 | 4/2006 | Brown | 2003/0236647 A1 | 12/2003 | Yoon et al. | |
| 7,039,449 B2 | 5/2006 | Al-Ali | 2004/0006261 A1 | 1/2004 | Swedlow et al. | |
| 7,043,289 B2 | 5/2006 | Fine et al. | 2004/0010188 A1 | 1/2004 | Wasserman et al. | |
| 7,047,054 B2 | 5/2006 | Benni | 2004/0024297 A1 | 2/2004 | Chen et al. | |
| 7,047,055 B2 | 5/2006 | Boaz et al. | 2004/0024326 A1 | 2/2004 | Yeo et al. | |
| 7,047,056 B2 | 5/2006 | Hannula et al. | 2004/0034293 A1 | 2/2004 | Kimball | |
| 7,060,035 B2 | 6/2006 | Wasserman | 2004/0039272 A1 | 2/2004 | Abdul-Hafiz et al. | |
| 7,062,307 B2 | 6/2006 | Norris et al. | 2004/0039273 A1 | 2/2004 | Terry | |
| 7,067,893 B2 | 6/2006 | Mills et al. | 2004/0054269 A1 | 3/2004 | Rantala et al. | |
| 7,072,701 B2 | 7/2006 | Chen et al. | 2004/0054291 A1 | 3/2004 | Schulz et al. | |
| 7,072,702 B2 | 7/2006 | Edgar, Jr. et al. | 2004/0059209 A1 | 3/2004 | Al-Ali et al. | |
| 7,079,880 B2 | 7/2006 | Stetson | 2004/0059210 A1 | 3/2004 | Stetson | |
| 7,083,593 B2 | 8/2006 | Stultz | 2004/0064020 A1 | 4/2004 | Diab et al. | |
| 7,085,597 B2 | 8/2006 | Fein et al. | 2004/0068164 A1 | 4/2004 | Diab et al. | |
| 7,096,052 B2 | 8/2006 | Mason et al. | 2004/0087846 A1 | 5/2004 | Wasserman | |
| 7,096,054 B2 | 8/2006 | Abdul-Hafiz et al. | 2004/0092805 A1 | 5/2004 | Yarita | |
| 7,107,088 B2 | 9/2006 | Aceti | 2004/0097797 A1 | 5/2004 | Porges et al. | |
| 7,113,815 B2 | 9/2006 | O'Neil et al. | 2004/0098009 A1 | 5/2004 | Boecker et al. | |
| 7,123,950 B2 | 10/2006 | Mannheimer | 2004/0107065 A1 | 6/2004 | Al-Ali et al. | |
| 7,127,278 B2 | 10/2006 | Melker et al. | 2004/0116788 A1 | 6/2004 | Chernoguz et al. | |
| 7,130,671 B2 | 10/2006 | Baker, Jr. et al. | 2004/0116789 A1 | 6/2004 | Boaz et al. | |
| 7,132,641 B2 | 11/2006 | Schulz et al. | 2004/0117891 A1 | 6/2004 | Hannula et al. | |
| 7,133,711 B2 | 11/2006 | Chernoguz et al. | 2004/0122300 A1 | 6/2004 | Boaz et al. | |
| 7,139,599 B2 | 11/2006 | Terry | 2004/0122302 A1 | 6/2004 | Mason et al. | |
| 7,142,901 B2 | 11/2006 | Kiani et al. | 2004/0133087 A1 | 7/2004 | Ali et al. | |
| 7,162,288 B2 | 1/2007 | Nordstrom | 2004/0133088 A1 | 7/2004 | Al-Ali et al. | |
| 7,190,987 B2 | 3/2007 | Lindekugel et al. | 2004/0138538 A1 | 7/2004 | Stetson | |
| 7,198,778 B2 | 4/2007 | Mannheimer et al. | 2004/0138540 A1 | 7/2004 | Baker, Jr. et al. | |
| 7,209,775 B2 | 4/2007 | Bae et al. | 2004/0143172 A1 | 7/2004 | Fudge et al. | |
| 7,215,984 B2 | 5/2007 | Diab et al. | 2004/0147821 A1 | 7/2004 | Al-Ali et al. | |
| 7,225,006 B2 | 5/2007 | Al-Ali et al. | 2004/0147822 A1 | 7/2004 | Al-Ali et al. | |

| | | | | | | |
|---|---|---|---|---|---|---|
| 2004/0147823 A1 | 7/2004 | Kiani et al. | EP | 0204259 | 12/1986 | |
| 2004/0147824 A1 | 7/2004 | Diab et al. | EP | 0430340 | 6/1991 | |
| 2004/0152965 A1 | 8/2004 | Diab et al. | EP | 0531631 | 3/1993 | |
| 2004/0158134 A1 | 8/2004 | Diab et al. | EP | 0724860 | 8/1996 | |
| 2004/0158135 A1 | 8/2004 | Baker, Jr. et al. | EP | 1986543 | 11/2008 | |
| 2004/0162472 A1 | 8/2004 | Berson et al. | FR | 2685865 | 7/1993 | |
| 2004/0171920 A1 | 9/2004 | Mannheimer et al. | JP | 7001273 | 11/1987 | |
| 2004/0171948 A1 | 9/2004 | Terry | JP | 2111343 | 4/1990 | |
| 2004/0176671 A1 | 9/2004 | Fine et al. | JP | 3245042 | 10/1991 | |
| 2004/0181133 A1 | 9/2004 | Al-Ali et al. | JP | 5049625 | 3/1993 | |
| 2004/0181134 A1 | 9/2004 | Baker, Jr. et al. | JP | 6014906 | 1/1994 | |
| 2004/0186358 A1 | 9/2004 | Chernow et al. | JP | 6029504 | 4/1994 | |
| 2004/0199063 A1 | 10/2004 | O'Neil et al. | JP | 6154177 | 6/1994 | |
| 2004/0204636 A1 | 10/2004 | Diab et al. | JP | 6269430 | 9/1994 | |
| 2004/0204637 A1 | 10/2004 | Diab et al. | JP | 3116259 | 6/1995 | |
| 2004/0204638 A1 | 10/2004 | Diab et al. | JP | 3116260 | 6/1995 | |
| 2004/0204639 A1 | 10/2004 | Casciani et al. | JP | 7236625 | 9/1995 | |
| 2004/0204865 A1 | 10/2004 | Lee et al. | JP | 7246191 | 9/1995 | |
| 2004/0210146 A1 | 10/2004 | Diab et al. | JP | 10216115 | 8/1998 | |
| 2004/0215069 A1 | 10/2004 | Mannheimer | JP | 10337282 | 12/1998 | |
| 2004/0230107 A1 | 11/2004 | Asada et al. | JP | 2000237170 | 9/2000 | |
| 2004/0230108 A1 | 11/2004 | Melker et al. | JP | 3134144 | 2/2001 | |
| 2004/0236196 A1 | 11/2004 | Diab et al. | JP | 2002224088 | 8/2002 | |
| 2004/0242980 A1 | 12/2004 | Kiani et al. | JP | 2003275192 | 9/2003 | |
| 2004/0249252 A1 | 12/2004 | Fine et al. | JP | 2004089546 | 3/2004 | |
| 2004/0257557 A1 | 12/2004 | Block et al. | JP | 2004329406 | 11/2004 | |
| 2004/0260161 A1 | 12/2004 | Melker et al. | JP | 2004329607 | 11/2004 | |
| 2004/0267103 A1 | 12/2004 | Li et al. | JP | 2004337605 | 12/2004 | |
| 2004/0267104 A1 | 12/2004 | Hannula et al. | JP | 2004344367 | 12/2004 | |
| 2004/0267140 A1 | 12/2004 | Ito et al. | JP | 2004351107 | 12/2004 | |
| 2005/0004479 A1 | 1/2005 | Townsend et al. | WO | WO8909566 | 10/1989 | |
| 2005/0010092 A1 | 1/2005 | Weber et al. | WO | WO9001293 | 2/1990 | |
| 2005/0020887 A1 | 1/2005 | Goldberg | WO | WO9111137 | 8/1991 | |
| 2005/0020894 A1 | 1/2005 | Norris et al. | WO | WO9502358 | 1/1995 | |
| 2005/0027207 A1 | 2/2005 | Westbrook et al. | WO | WO9736536 | 10/1997 | |
| 2005/0033128 A1 | 2/2005 | Ali et al. | WO | WO98/57577 | 12/1998 | |
| 2005/0033129 A1 | 2/2005 | Edgar, Jr. et al. | WO | 9947039 | 9/1999 | |
| 2005/0043599 A1 | 2/2005 | O'Mara | WO | WO9947039 | 9/1999 | |
| 2005/0043600 A1 | 2/2005 | Diab et al. | WO | 0028888 | 5/2000 | |
| 2005/0049470 A1 | 3/2005 | Terry | WO | 0059374 | 10/2000 | |
| 2005/0049471 A1 | 3/2005 | Aceti | WO | WO03039326 | 5/2003 | |
| 2005/0075550 A1 | 4/2005 | Lindekugel | WO | WO2005010567 | 2/2005 | |
| 2005/0113651 A1 | 5/2005 | Wood et al. | WO | WO2005010568 | 2/2005 | |
| 2005/0175540 A1 | 8/2005 | Oraevsky et al. | WO | 2005025399 | 3/2005 | |
| 2005/0177034 A1 | 8/2005 | Beaumont | WO | 2005110215 | 11/2005 | |
| 2005/0182389 A1 | 8/2005 | Laporte et al. | WO | 2006097910 | 9/2006 | |
| 2005/0197548 A1 | 9/2005 | Dietiker | WO | 2006109072 | 10/2006 | |
| 2005/0228248 A1 | 10/2005 | Dietiker | | | | |
| 2005/0251056 A1 | 11/2005 | Gribkov et al. | | | | |
| 2005/0277819 A1 | 12/2005 | Kiani et al. | | | | |
| 2005/0283059 A1 | 12/2005 | Iyer et al. | | | | |
| 2006/0058594 A1 | 3/2006 | Ishizuka et al. | | | | |
| 2006/0084852 A1 | 4/2006 | Mason et al. | | | | |
| 2006/0089547 A1 | 4/2006 | Sarussi | | | | |
| 2006/0106294 A1 | 5/2006 | Maser et al. | | | | |
| 2006/0122475 A1 | 6/2006 | Balberg et al. | | | | |
| 2006/0195028 A1 | 8/2006 | Hannula et al. | | | | |
| 2006/0224058 A1 | 10/2006 | Mannheimer | | | | |
| 2006/0247501 A1 | 11/2006 | Ali | | | | |
| 2006/0247506 A1 | 11/2006 | Balberg et al. | | | | |
| 2006/0258921 A1 | 11/2006 | Addison et al. | | | | |
| 2006/0276700 A1 | 12/2006 | O'Neil | | | | |
| 2007/0032710 A1 | 2/2007 | Raridan et al. | | | | |
| 2007/0032712 A1 | 2/2007 | Raridan et al. | | | | |
| 2007/0032715 A1 | 2/2007 | Eghbal et al. | | | | |
| 2007/0073121 A1 | 3/2007 | Hoarau et al. | | | | |
| 2007/0073125 A1 | 3/2007 | Hoarau et al. | | | | |
| 2007/0073126 A1 | 3/2007 | Raridan, Jr. et al. | | | | |
| 2007/0073128 A1 | 3/2007 | Hoarau et al. | | | | |
| 2007/0129622 A1 | 6/2007 | Bourget et al. | | | | |
| 2007/0129769 A1 | 6/2007 | Bourget et al. | | | | |
| 2007/0142715 A1 | 6/2007 | Banet et al. | | | | |
| 2007/0142717 A1 | 6/2007 | Lowery et al. | | | | |
| 2007/0208269 A1 | 9/2007 | Mumford et al. | | | | |
| 2008/0312533 A1 | 12/2008 | Balberg et al. | | | | |

FOREIGN PATENT DOCUMENTS

| | | |
|---|---|---|
| DE | 19632361 | 2/1997 |
| EP | 0127947 | 12/1984 |

OTHER PUBLICATIONS

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Buschman, J.P., et al.: "Principles and Problems of Calibration of Fetal Oximeters," *Biomedizinische Technik*, vol. 42, pp. 265-266 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKocK, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919, 1998.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Bio. Soc.*, 1998.

Ferrell, T.L., et al.; "Medical Telesensors," *SPIE*, vol. 3253, pp. 193-198 (1998).

Ikeda, Kenji, et al.; "Improvement of Photo-Electric Plethysmograph Applying Newly Developed Opto-Electronic Devices," *IEEE Tencon*, pp. 1109-1112 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summ.

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, P. A., et al.; "Investigation of esophageal photoplethysmographic signals and blood oxygen saturation measurements in cardiothoracic surgery patients," *Physiological Measurement*, vol. 23, No. 3, pp. 533-545 (Aug. 2002).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Bentley, David J. et al.; "Measure Pressure with Thin Film"; Paper Film & Foil Converter; May 1, 2003.

Reuss, James L.; "Factors Influencing Fetal Pulse Oximetry Performance," *Journal of clinical Monitoring and Computing*, vol. 18, pp. 13-14 (2004).

Wendelken, Suzanne, et al.; "The Feasibility of Using a Forehead Reflectance Pulse Oximeter for Automated Remote Triage," *IEEE*, pp. 180-181 (2004).

Urquhart, C., et al.; "Ear probe pulse oximeters and neonates," *Anesthesia*, vol. 60, p. 294 (2005).

* cited by examiner

SYSTEM AND METHOD FOR ATTACHING A SENSOR TO A PATIENT'S SKIN

RELATED APPLICATIONS

This application claims priority to U.S. Provisional Application No. 61/009,355, filed Dec. 28, 2007, and is incorporated herein by reference in its entirety.

BACKGROUND

The present disclosure relates generally to pulse oximetry and more particularly, to a method and system for affixing a sensor to a patient's skin while obtaining a spectrophotometric measurement.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the oxygen saturation of hemoglobin in arterial blood, the volume of individual blood pulsations supplying the tissue and/or the rate of blood pulsations corresponding to each heartbeat of a patient.

Pulse oximeters may utilize a non-invasive sensor that transmits light through a patient's tissue and that photoelectrically senses the absorption and/or scattering of the transmitted light in such tissue. Physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms. Changes in the amount of arterial blood in the tissue during a blood pressure pulse may change the amount and character of the light detected by the sensor's photodetector.

Pulse oximetry sensors may be placed on a patient in a location that is normally perfused with arterial blood to facilitate proper light absorption. The most common sensor sites include a patient's fingertips, toes, or earlobes. However, in patients such as newborn babies, placement of the sensor on such anatomical sites may be difficult or infeasible. Further, postpartum oxygen saturation measurements of a newborn may be needed expeditiously for sustained periods of time. However, immediately after exiting a womb, a newborn's skin may be partially, or even completely, covered with fluids, such as amniotic fluid, meconium, vernix, and/or blood. This may hinder proper attachment of a sensor to the newborn, and/or make it difficult to keep the sensor affixed to the newborn.

SUMMARY

Certain aspects commensurate in scope with the disclosure are set forth below. It should be understood that these aspects are presented merely to provide the reader with a brief summary of certain embodiments and that these aspects are not intended to limit the scope of the disclosure. Indeed, the disclosure may encompass a variety of aspects that may not be set forth below.

In an embodiment, there is provided a spectrophotometric sensor. In an embodiment, the sensor includes a light emitter disposed in a light barrier, one or more photodetectors disposed outside the light barrier, and a light scattering medium configured to contact a tissue site, wherein the light scattering medium is capable of increasing the effective detection area of the one or more photo detectors.

In an embodiment, there is provided a spectrophotometric sensor. In an embodiment, the sensor includes a photodetector disposed in a light barrier, one or more light emitters outside the light barrier, and a light scattering medium configured to contact a tissue site, where the light scattering medium is capable of increasing the effective emission area of the one or more light emitters.

In an embodiment, there is provided a spectrophotometric sensor. In an embodiment, the sensor includes a sensor body, and one or more light emitters and one or more photodetectors. In an embodiment) the sensor farther includes a light scattering medium capable of increasing at least one of the effective detection area of the one or more photodetectors or the effective emission area of the one or more light emitters, wherein the light scattering medium is capable of forming a patient contact surface of the spectrophotometric sensor.

In an embodiment, there is provided a method for assembling a sensor. In an embodiment, the method includes providing a sensor body, providing one or more light emitters and providing one or more photodetectors. In an embodiment, the method further includes providing a light scattering medium capable of use as a patient contacting surface, wherein the light scattering medium is capable of increasing at least one of the effective detection area of the one or more photodetectors or the effective detection area of the one or more light emitters.

In an embodiment, there is provided a method of applying a spectrophotometric sensor. In an embodiment the method includes applying a spectrophotometric sensor having a light scattering gel to a wet tissue site of a patient such that the light scattering gel adheres to the wet tissue site.

BRIEF DESCRIPTION OF THE DRAWINGS

Advantages of the disclosure may become apparent upon reading the following detailed description and upon reference to the drawings in which.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Pulse oximetry sensors are typically placed on a patient in locations, such as tissue sites, that facilitate suitable light transmission and absorption. The most common sensor sites include a patient's fingertips, toes, or earlobes, among others. In newborns, such anatomical regions may be inconvenient and/or unsuitable for attaching a pulse oximetry sensor. Therefore, alternate tissue sites/regions well perfused with blood may be chosen for placement of the pulse oximetry sensor. In newborns, anatomical regions or sites comprising surfaces that are flat, such as a back (scapula) area, a hip (iliac) region, a forehead, etc. may be preferable for attaching a pulse oximetry sensor. Furthermore, while using a spectrophotometric pulse oximetry method, it may be desirable to optimize the optical coupling of the pulse oximetry sensor to the anatomical regions the sensor is affixed thereon. Accordingly, tiny anatomical dimensions of a newborn coupled with its wet skin postpartum may make it preferable to use a "reflectance type" pulse oximetry sensor in order to optimize a pulse oximetry measurement.

Reflectance type pulse oximetry sensors may include an emitter and a detector that may be placed on the same side of the sensor site. If for example, the tissue site on which the sensor is placed includes a back area, the sensor may be positioned such that the emitter and detector lay on the same side of the sensor site, namely, the back. During operation, the emitter emits one or more wavelengths of light at tissue sites/regions of the back. The light may be transmitted into the tissue and some portion of the light diffusely scatters through the tissue to a nearby detector on the sensor. The detected light may be processed to determine various physiological characteristics of the patient. For determining the oxygen saturation of the patient's arterial blood, two or more wavelengths of light may be used, most commonly red and near infrared wavelengths.

Figure 1A:
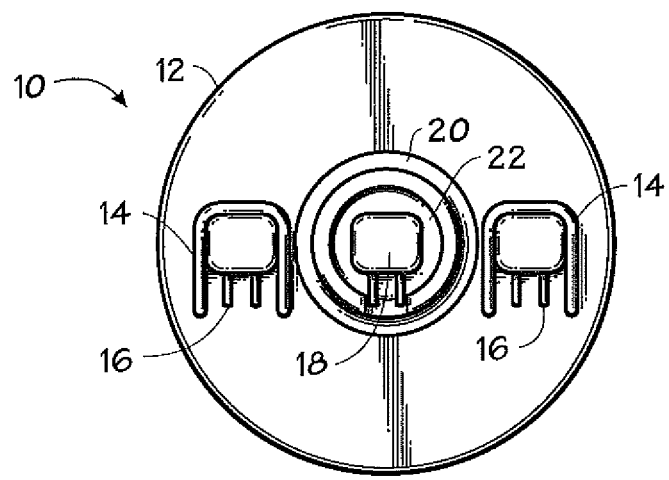
FIG. 1A is a top view of a sensor assembly in accordance with an embodiment.
Figure 1B:
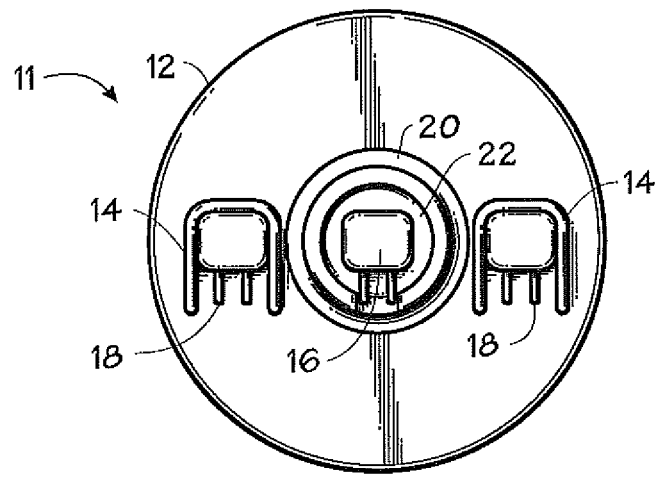
FIG. 1B is a top view of another sensor assembly in accordance with an embodiment.

Turning to FIGS. 1A and 1B, a top view of a reflectance type pulse oximetry sensor assembly 10 in accordance with an embodiment is illustrated. The figure illustrates a top view of multiple components comprising the sensor assembly 10. The components of the sensor assembly 10 may be modular, one piece, and/or custom built according to operational requirements. The components comprising the sensor assembly 10 are disposed on a sensor substrate 12 having a central region and an outer region, which are capable of providing support for sensor assembly components. According to an embodiment, the components may include optical component slots 14 disposed on or within the substrate 12 which secure optical components, such as detectors 16 or emitter 18 (as shown in FIGS. 1A and 1B, respectively) to the sensor substrate 12. In an embodiment, the slots 14 may be placed on the substrate 12 such that they are flush with the surface of the substrate 12. In such an embodiment, the sensor assembly 10 may maintain a generally minimal thickness, which may be desirable for light coupling efficiency when fitted with the optical components 16 or 18.

In an embodiment, the sensor substrate 12 may be configured to house an optical barrier 20, and a light pipe 22 disposed in a central region of the substrate 12. The portion of the sensor substrate 12 opposite the optical components may be capable of providing a surface on which an adhesive may be disposed. The adhesive may be of safely affixing the sensor assembly 10 adjacent a tissue site, such as on a patient's skin, and may also be capable of providing light scattering structure for light emitted by the emitter, as well as for light reflected from the patient's tissue. Accordingly, in one embodiment, the bottom portion of the sensor substrate 12 may be roughened or textured to better facilitate a uniform scattering of the light through the adhesive.

In an embodiment, the sensor substrate 12 is shown as being a generally circular in shape. However, it should be appreciated that the shape of the substrate 12 may vary according to system requirements and constraints. Further, in some embodiments the substrate 12 may be opaque, however, in other embodiments the substrate 12 may be light-transmissive, enabling light to propagate efficiently therethrough.

As noted above, the optical components in one embodiment may include an emitter 18 and a detector 16. Thus, the emitter 18 may comprise a light emitting diode LED, delivering electromagnetic radiation, such as light of a specified wavelength, to a patient's tissue via the light pipe 22 in FIG. 1A. Optical barrier 20 may be capable of optically separating the emitter 18 from the detector 16. Thus, the optical barrier 20 may be capable of significantly attenuating or eliminating the amount of light propagating directly between the emitter 18 and the detector 16. This is desirable since light propagating through the light pipe 22 may be first guided to the tissue for absorbance/scattering before reaching the detectors 16. This may improve the signal to noise ratio of the pulse oximetry measurement, increasing its reliability. Accordingly, the optical barrier 20 may be composed of light absorbing or reflecting material, and be capable of preventing shunting between the emitter 18 and the detector 16.

The light pipe 22 may also be capable of facilitating optical matching in order to maximize the amount of light delivered to the tissue from the emitter 18. In one embodiment, the light pipe 22 may also be capable of providing a method and system capable of securing the emitter 18 (or detector 16 in the embodiment of FIG. 1B) to the sensor assembly 10 via a clear adhesive, such as a clear epoxy. Using such an adhesive may enhance the optical coupling between the optical component and the light pipe 22.

In an embodiment, the slots 14 used to secure the detector 16 may be offset from the emitter 18 as shown in FIG. 1A. In the embodiment illustrated in FIG. 1A, only two detectors are shown. However, it may be possible to increase the amount of detectors 16 affixed to the sensor assembly 10 by adding more detector slots, such as the slots 14, to the substrate 12. This may increase the detection area of the sensor 10, and increase the signal to noise ratio of a pulse oximetry measurement. Alternatively, a single slot 14 and associated detector 16 may be provided to simplify design and construction of the sensor 10.

FIG. 1B illustrates an embodiment of a sensor assembly 11 comprising similar modular components as those shown in FIG. 1A. In the embodiment depicted in FIG. 1B, the positions of the emitter 18 and the detector 16 are exchanged. Accordingly, this configuration comprises a single centrally disposed detector 16 affixed adjacent the light pipe 22, and two emitters 18 disposed generally laterally adjacent to the detector 16. In this embodiment, optical component slots 14 may be capable of securing the emitters 18 to the surface substrate 12. The optical barrier 20 may increase the amount of light received at the detector 16 passes through at least a portion of patient's tissue rather than traveling directly from the adjacent emitters 18. The light pipe 22, in this configuration, may further provide an optical matching medium for maximizing the amount of light propagating from the tissue to the detector 16. This, too, may enhance the signal to noise ratio and reliability of the pulse oximetry measurement.

Although two emitters are shown in FIG. 1B, it should be appreciated that the sensor substrate 12 may accommodate additional optical component slots 14 (as was the case for the sensor assembly 10) for securing additional emitters, such as emitter 18. This may increase the light emission area of the sensor, and may increase the amount of light illuminating the tissue and, may improve the pulse oximetry measurement. Similarly, a single optical component slot 14 and associated emitter 18 may be provided, if desired.

Figure 2:
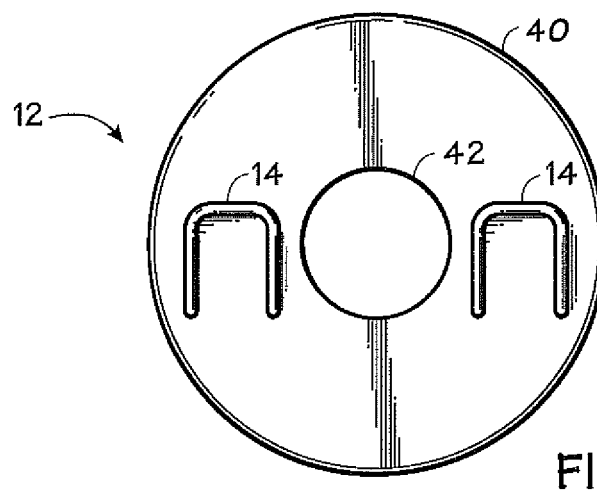
FIG. 2 is a top view of a sensor substrate in accordance with an embodiment.

Turning now to FIG. 2, a top view of the sensor substrate 12 in accordance with an embodiment is illustrated. In an embodiment the sensor substrate 12 comprises an outer portion 40 and a central opening 42. The central opening 42 may be capable of securing the optical barrier 20 and the light pipe 22 adjacent the sensor assembly 10 and 11. The outer portion 40 of the sensor substrate 12 may be capable of supporting optical slots 14, designated for securing the optical components, such as detectors 16 or emitter 18.

In an embodiment, the bottom side of the outer portion 40 may be capable of supporting a viscous medium or an adhesive for affixing the sensor to a tissue site of a patient. Using an adhesive, such as a hydrogel, or other form of hydrocolloid, may be desirable since it may not damage the skin, yet may be strong enough to maintain the sensor on the patient's body throughout a prolonged monitoring period. In situations where the tissue site, such as the skin of a baby, is wet the water absorbing properties of the hydrogel may facilitate adhering of the sensor to the tissue. Further, the hydrogel may be translucent and may have light scattering characteristics, making the hydrogel suitable for propagating light to and from the sensor and/or the tissue.

Accordingly, to the extent light diffusely scatters throughout the hydrogel, it may be possible to increase the detection area of the detectors 16 when those are disposed along a generally annular region of the substrate 12. Similarly, in embodiments where emitters 18 are disposed along the annular region of the substrate 12, the hydrogel may increase the emission area of the emitters 18. Aside from hydrogel, the above mentioned features and light-scattering characteristics may also be achievable by substances, which are highly viscous, semisolid, viscid, and/or gelatinous and which may be used to affix the sensor 10 adjacent a patient's skin.

Figure 3A:
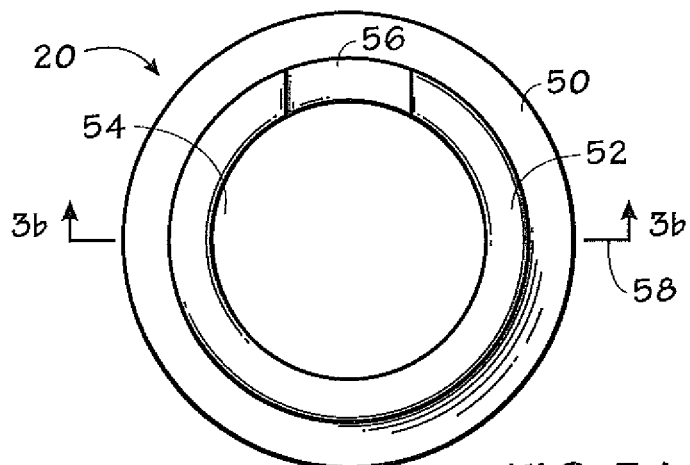
FIG. 3A is a top view of an optical barrier in accordance with an embodiment.
Figure 3B:
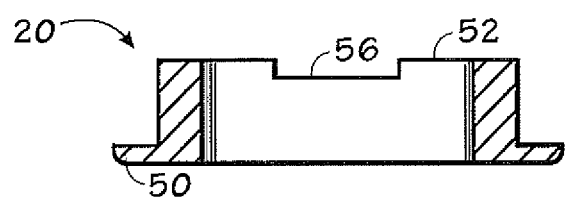
FIG. 3B is a cross-sectional view of the optical barrier taken along sight line 3B in accordance with an embodiment.

Turning now to FIGS. 3A and 3B, an optical barrier 20 in accordance with an exemplary embodiment. These figures respectively depict a top and a cross-sectional view (as seen by sight line 3b in FIG. 3A) of the optical barrier 20. As discussed above, the optical barrier 20 may be capable of attenuating light so that a reduced amount, or no light may propagate directly between the emitter 18 and the detector 16 (FIGS. 1A, 1B). For light to be absorbed by the optical barrier 20, the optical barrier 20 may comprise an opaque material, such as plastic, metal, ceramic, or composite materials. Alternatively, the optical barrier 20 may comprise a reflective material, such as aluminum, for achieving the same purpose.

In the embodiment of FIGS. 3A and 3B, the optical barrier 20 may include a generally cylindrical shape with a hollow interior 54. The hollow interior 54 may be adapted to securely circumscribe the light pipe 22. Thus, the hollow interior 54 may be capable of guiding the light traveling either to or from the optical components, i.e., emitters 18 or detectors 16. In this embodiment, optical barrier 20 may further have a bottom portion 50 and a top portion 52, such that the bottom portion 50 has a generally greater width than the top portion 52. Such a structural configuration may provide for the secure attachment of the optical barrier 20 to the substrate 12. In an embodiment, the optical barrier 20 may include a cut out 56 capable of supporting a light pipe 22, which may be associated with an emitter 18 or detector 16. In particular, the cut out 56 may be configured to accommodate lead wires of the emitter 18 or detector 16, so that the lead wires are structurally protected when the above-mentioned sensor assemblies 10 and/or 11 are in use.

Figure 4A:
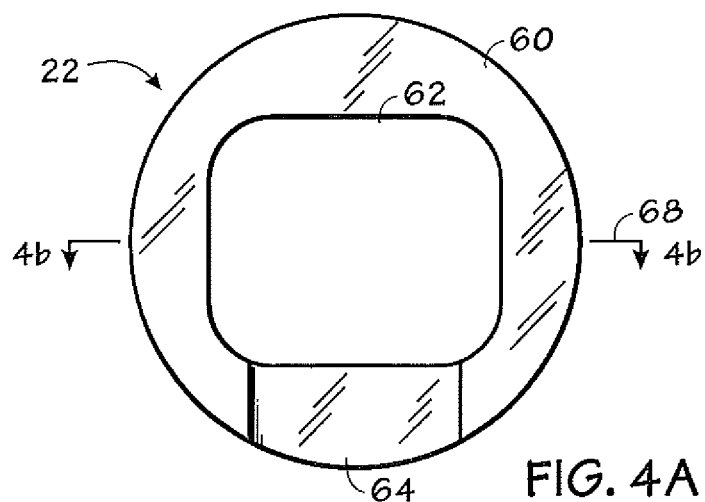
FIG. 4A is a top view of a light pipe in accordance with an embodiment.
Figure 4B:
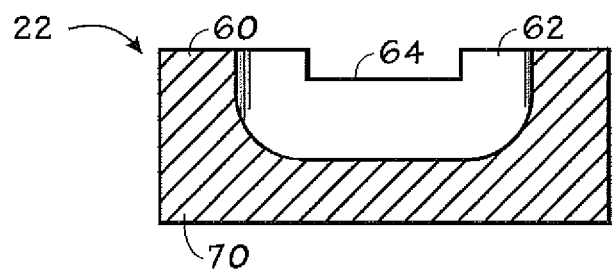
FIG. 4B is a cross-sectional view of a light pipe taken along sight line 4B in accordance with an embodiment.
Figure 4C:
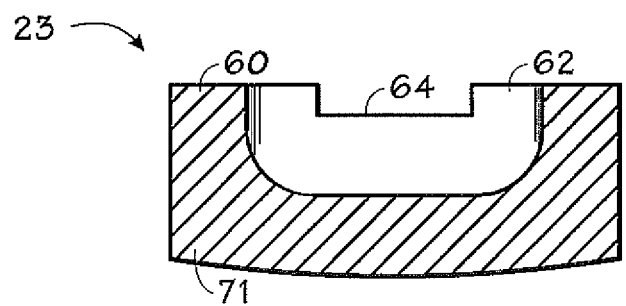
FIG. 4C is a cross sectional view of a light pipe in accordance with an embodiment.

Turning now to FIGS. 4A-4C, a light pipe 22 in accordance with an embodiment is shown. In this embodiment, the light pipe 22 may be capable of providing an optical pathway for the light to and from the optical components. The light pipe 22 may also be capable of optically coupling optical components, i.e., the emitter 18 or detector 16, to the adjacent tissue site, such as skin. This may increase the amount of light delivered to the tissue from the emitter 18, and/or received from the tissue by the detector 16. Hence, it may be desirable for the light pipe 22 to comprise of a light-transparent material, such as acrylic. The light pipe 22 may also be comprised of air, such that the medium through which light propagates from the emitter 18 to the patient's tissue is air.

In the depicted embodiment, the light pipe 22 has an outer portion 60 and an inner portion 62 for housing the optical components, i.e., the emitter 18 or detector 16. The embodiment may further include a notch 64 disposed on the top of the light pipe 22. Notch 64 may be capable of providing sufficient space for wires leading to the optical components of the sensor assemblies 10 and 11. In an embodiment, notch 64 may correspond to cut out 56 of the optical barrier 20 of FIGS. 3A and 3B, and may provide a stable fitting between the light pipe 22 and the optical barrier 20.

FIG. 4B illustrates a cross-sectional view of the light pipe 22, as shown from the perspective view indicated by sight line 4b of FIG. 4A. FIG. 4C depicts an embodiment of a light pipe 23 having similar configuration to the light pipe 22. Rather than having a flat bottom surface, such as the one shown by surface 70 of the light pipe 22, the light pipe 23 has a curved bottom surface 71. Such a configuration may be suitable for improving coupling between the sensor assembly 10, 11 and the skin in situations where the sensor 10, 11 is attached to anatomical regions that are generally curved or not flat or planar. As will be appreciated by those of ordinary skill in the art, the skin contacting surface of the light pipe 22 may be shaped based on operational and/or clinical requirements such as these.

Figure 5A:
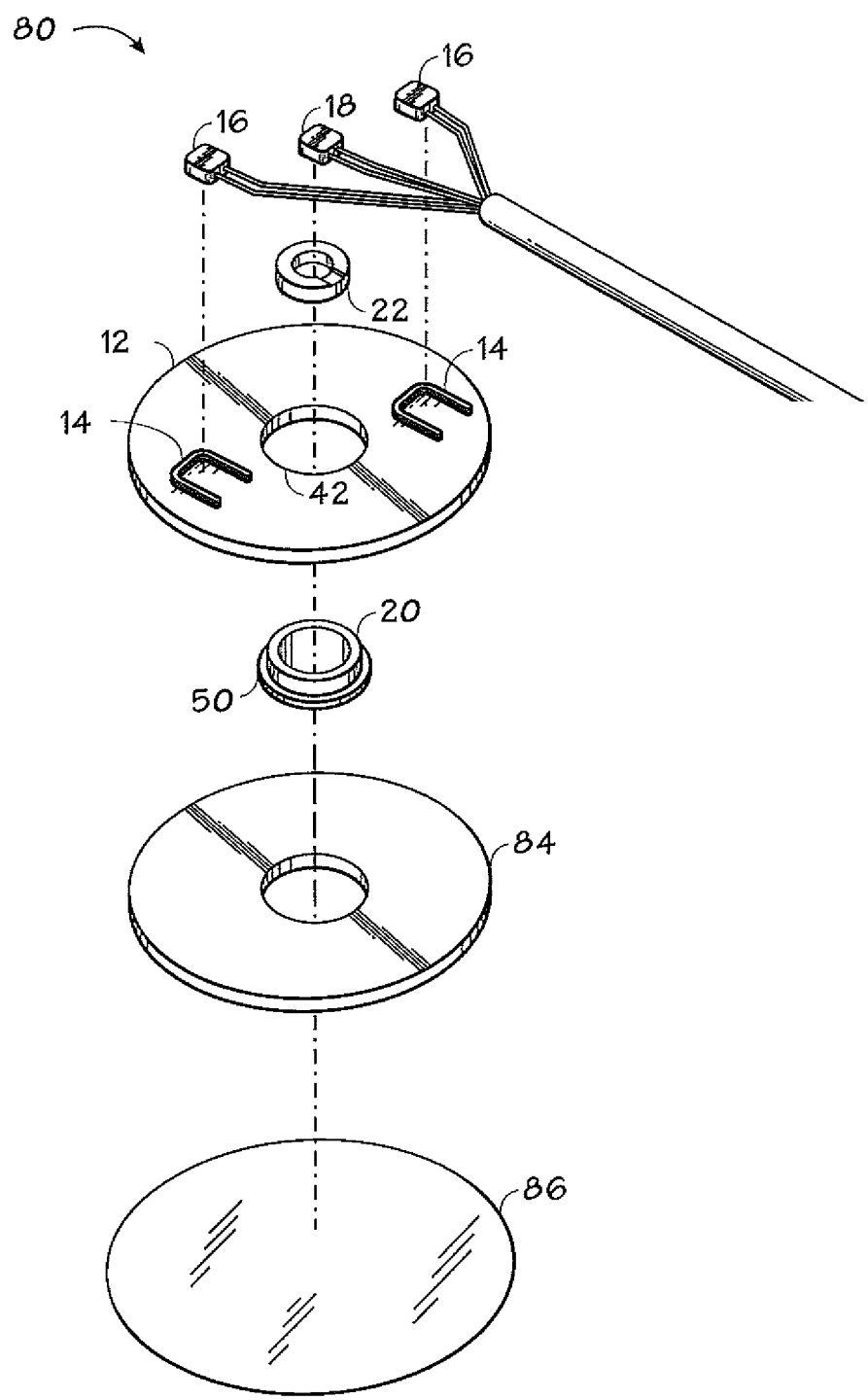
FIGS. 5A and 5B are exploded views of a baby sensor in accordance with another embodiment.

FIG. 5A depicts an exploded view of a pulse oximetry sensor 80 in accordance with an embodiment. In the illustrated embodiment, the substrate 12 is light transmissive such that light signals may propagate therethrough. Such a substrate 12 may be capable of enabling positioning detectors 16 within optical components slots 14. This positioning may enable light to propagate via the substrate 12 to the detectors 16 as it reflects from the patient's tissues.

As further illustrated, in this embodiment, emitter 18 is disposed between the detectors 16 and is capable of being positioned within the light pipe 22. The light pipe 22 containing the emitter 18 may be generally centrally disposed within the optical barrier 20, which in turn may be positioned within the central hole 42 of the sensor substrate 12. In this embodiment, the optical barrier 20 is fitted within the central hole 42, such that the lower portion 50 of the optical barrier 20 generally abuts the bottom part of the sensor substrate 12. Adhesive member 84 shaped as a ring formed of a translucent material, such as hydrogel, may be affixed to the bottom portion of the sensor substrate 12 so that the member 84 generally does not cover the center opening 42 and generally surrounds the lower portion 50 of the optical barrier 20.

In an exemplary mode of operation, light emitted by emitter 18 propagates through the light pipe 22 and impinges the tissue without propagating through the adhesive member 84. The light barrier 20 ensures that most or all of the light emitted by the emitter 18 reaches the tissue and is not shunted to the detectors 16 via the adhesive member 84. Light re-emitted from the tissue propagates through the adhesive member 84 with a portion of it reaching the detectors 16. Light scatter by the adhesive member 84 may increase the amount of light reaching the detector 16, making for a better pulse oximetry signal since the area of the scattering adhesive is substantially larger than the area of the detector itself. Furthermore, the enlarged surface area from which the light reemerges and can reach the photodetector may provide a larger tissue volume over which the measured signals derive. Non-uniform signal strengths and/or light intensities over the tissue surface area may become more reliably detected and less dependent on precise sensor placement. As can be appreciated, similar benefits can be achieved when the position of the light emitter 18 and detector 16 are exchanged.

In an embodiment packaging of the sensor 80 may incorporate a releasable or removable protective layer or film 86 covering the adhesive layer 84. Accordingly, the protective layer 86 is adhered to the face of the adhesive 84 adapted to be placed on the patient. In such embodiments, the release layer may be capable of being removed prior to applying the sensor 80 to the tissue site. Such a release layer may protect the integrity of the adhesive member 84 prior to use. This may extend the lifetime of the adhesive 84 when the sensor assembly 12 is not in use and/or stored.

Figure 5B:
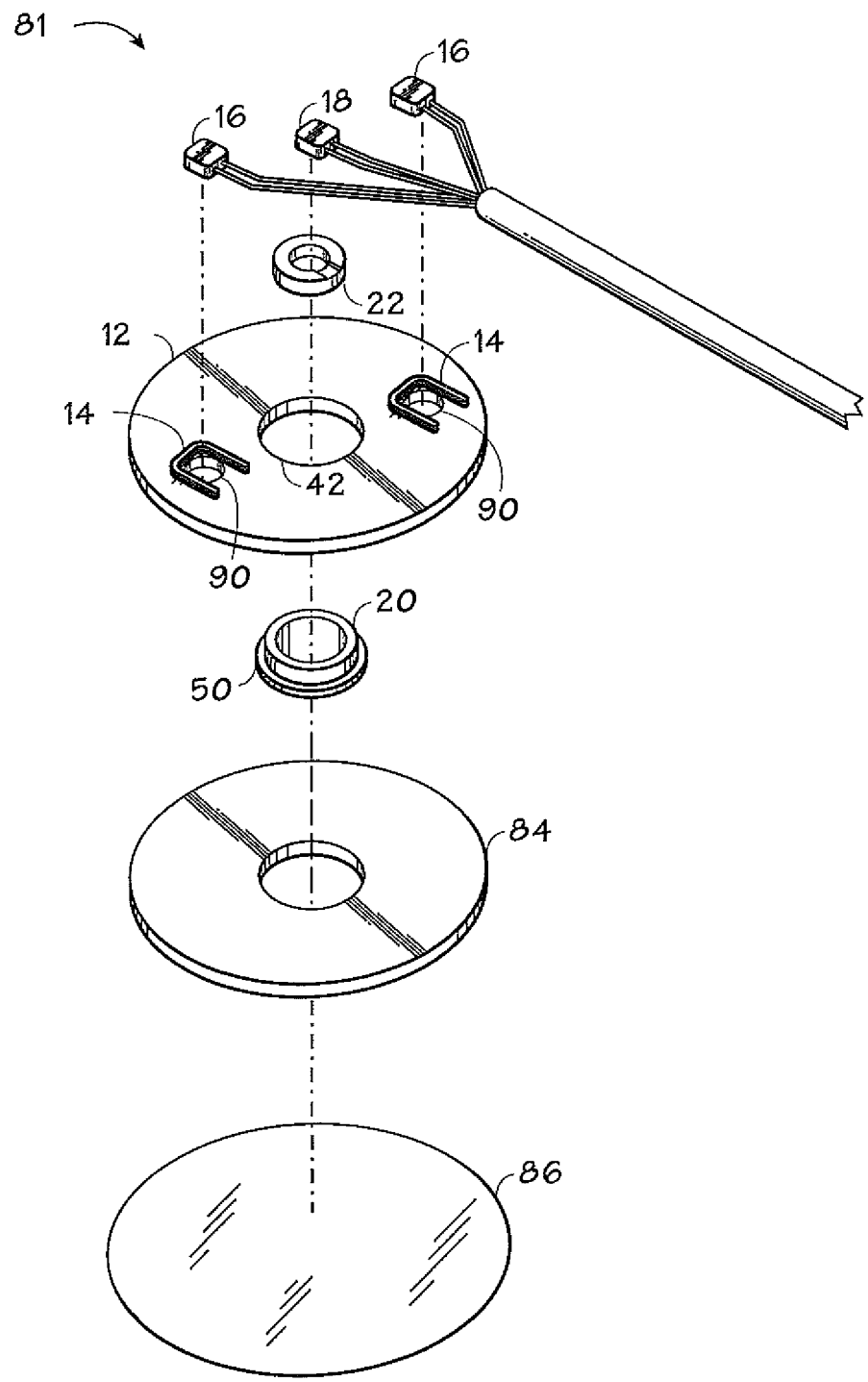

FIG. 5B illustrates an exploded view of a sensor 81 having components similar to the sensor 80 but for the substrate 12, and optical component slots 14. In this embodiment, the substrate 12 may include openings 90 to facilitate optical transmission between the patient's skin and the detectors 16 which, in the illustrated embodiment, are disposed within the optical components slots 14. Thus, the detectors 16 may be positioned within the slots 14 such that light may propagate directly from the patient's skin to the detectors 16 via the holes 90. In such an embodiment, the substrate 12 may or may not be light transmissive.

Figure 6A:
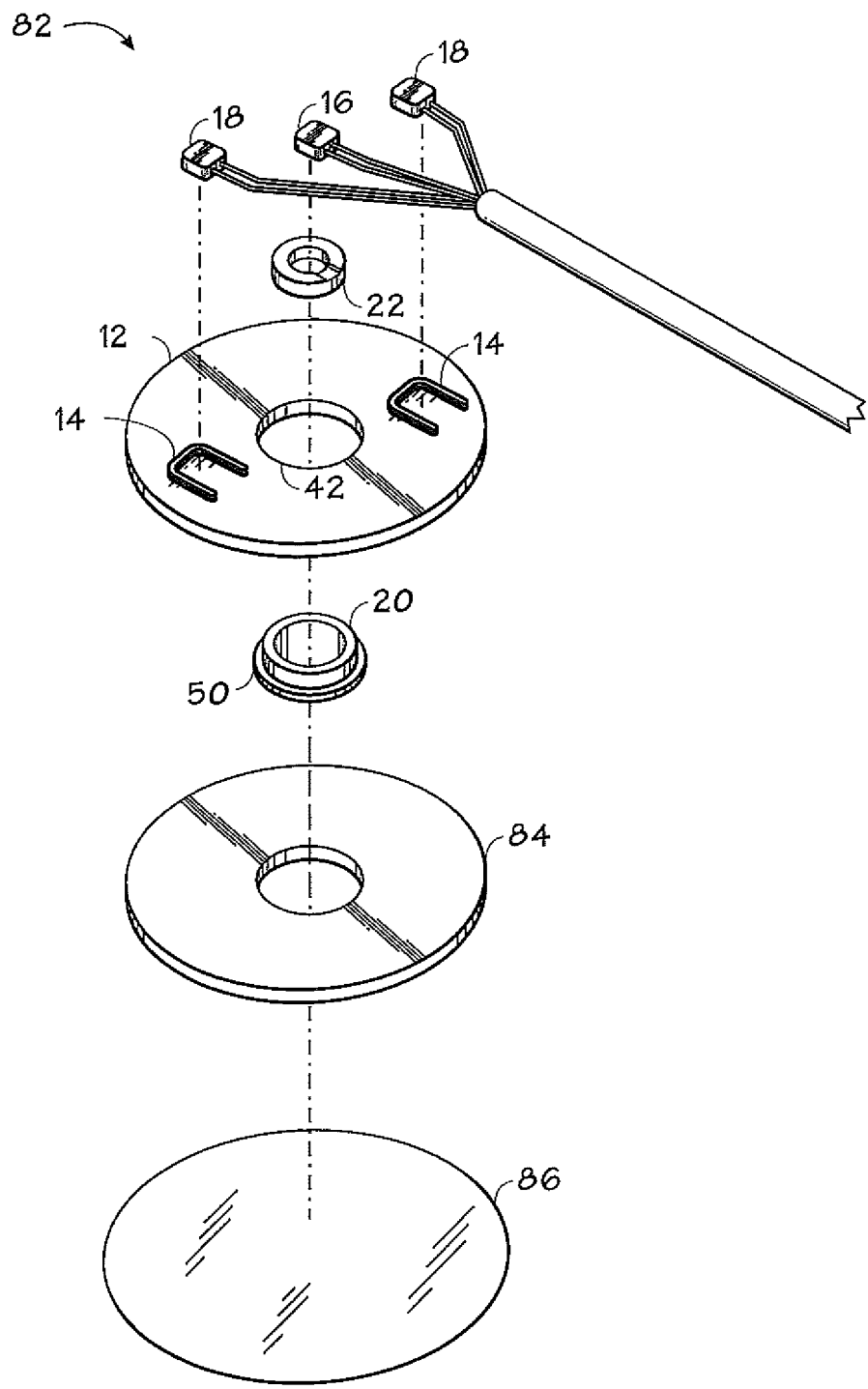
FIGS. 6A and 6B are exploded views of a baby sensor in accordance with alternative embodiment.

FIG. 6A is an exploded view of a sensor 82 in accordance with an embodiment of. The embodiment shown in the figure depicts similar sensor components shown in FIG. 5A with the positions of the emitter 18 and the detector 16 exchanged. In this embodiment, the substrate 12 may be light transmissive such that light signals may propagate therethrough. Such a substrate may be configured to enable positioning the emitters 18 within optical components slots 14 so that light may propagate via the light transmissive substrate 12 to the patient's skin, and from there may be reflected to the detector 16.

In this embodiment, the sensor assembly 82 includes two radially disposed emitters 18 and a centrally disposed detector 16. In an exemplary mode of operation, light emitted by the emitters 18 propagates through the light transmitting adhesive 84. In so doing, the adhesive 84 may be capable of scattering the light onto a relatively large surface area of the skin/tissue. Consequently, more light may reach the skin/tissue, which may increase the amount of light reflected to the detector 16. The optical barrier 20 increase the likelihood that reflected light propagating through or within the light pipe 22 is emerging from the tissue and is not directly received from the emitters 18. In this manner, shunting is reduced and/or prevented, which may improve the signal to noise ratio of the signal measurement.

Figure 6B:
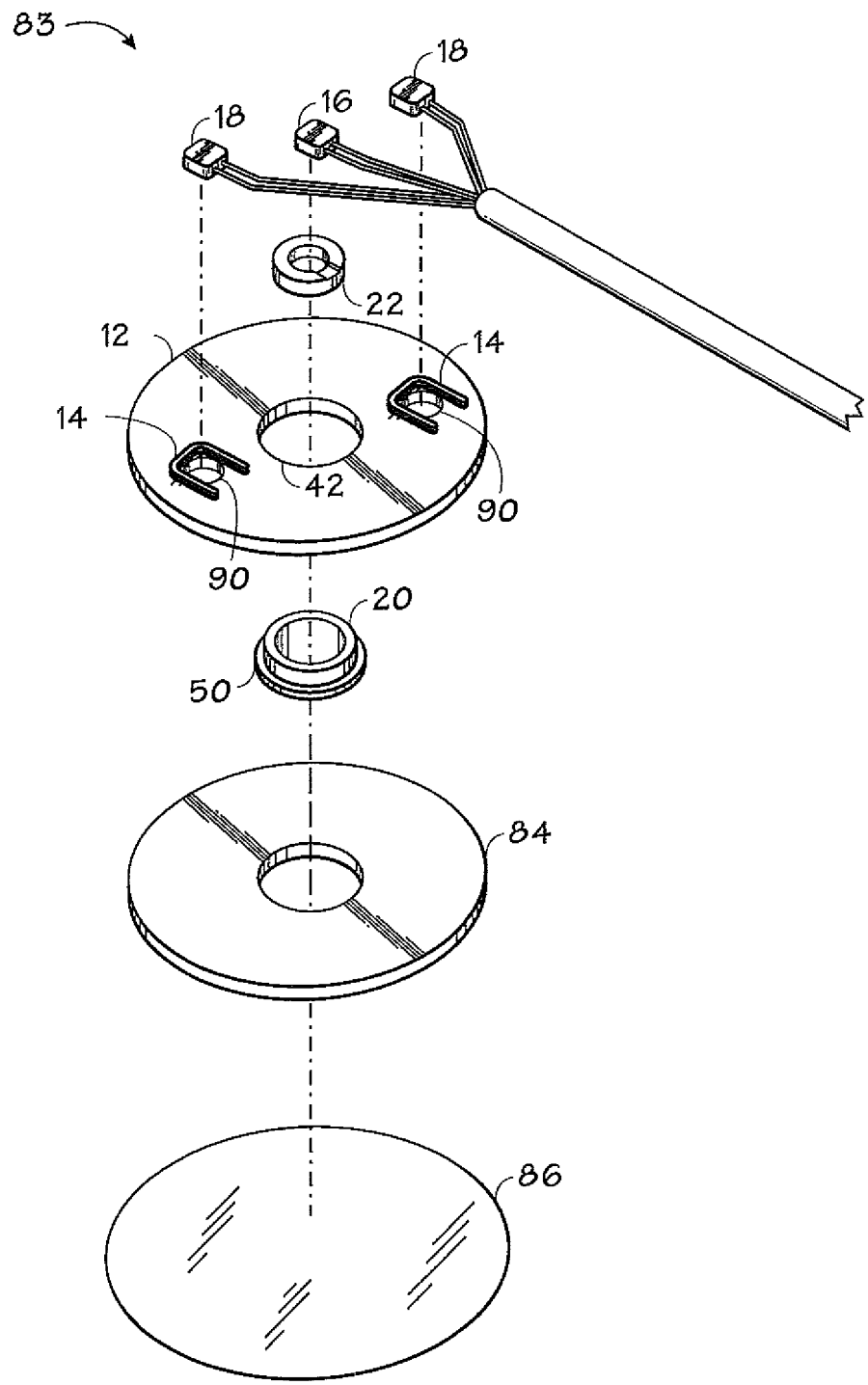

FIG. 6B illustrates an exploded view of a sensor 83 having components similar to the sensor 82 but for the substrate 12 and optical component slots 14. In this embodiment, the substrate 12 may include openings 90 capable of allowing optical transmission between the patient's skin and the emitters 18 in the optical components slots 14. In this embodiment the emitters 18 may be positioned within the slots 14 such that light may travel directly from the emitters 18 to the tissue site, i.e., patient's skin via the holes 90. In such an embodiment, the substrate 12 may or may not be light transmissive.

Figure 7:
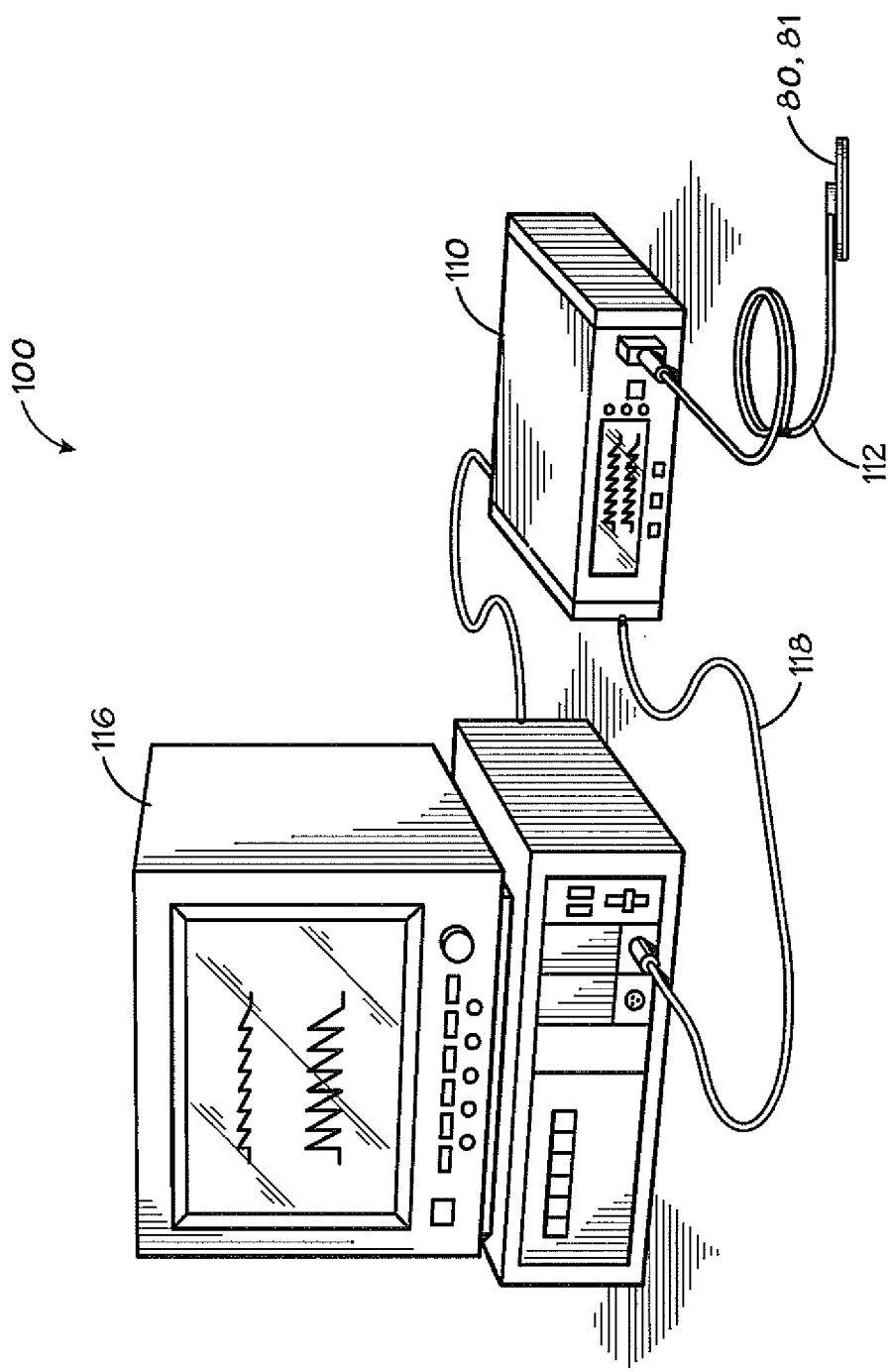
FIG. 7 is a pulse oximetry system coupled to a multi-parameter patient monitor in accordance with an embodiment.

The pulse oximetry sensors 80-83 may be configured to be coupled directly to a pulse oximetry system 100 shown in FIG. 7. In an embodiment the system 100 includes a monitor 110 capable of being connected to a computer or multipurpose monitor 116 via cable 118. The monitor 110 is also capable of being connected to the pulse oximetry sensor 80-83 via cable 112. However, it should be appreciated that the sensor 80-83 or cable 112 may be coupled to a transmission device (not shown) to facilitate wireless transmission between the sensor 80-83 and monitor 110. The monitor 110 may be any suitable pulse oximeter, such as those available from Nellcor Puritan Bennett, LLC, and/or Covidien.

As will be appreciated the disclosed embodiments referencing pulse oximetry sensors, systems and techniques are merely illustrative of one suitable spectrophotometric technique for which the present sensors are suitable. The present sensors and techniques however, may be used in other spectrophotometric applications.

While the disclosure may be suitable to various modifications and alternative forms, embodiments have been shown by way of example in the drawings and have been described in detail herein. However, it should be understood that the disclosure is not intended to be limited to the particular forms disclosed. Rather, the disclosure is intended to encompass all modifications, equivalents, and alternatives falling within the spirit and scope of this disclosure as defined by the following appended claims.

The invention claimed is:

1. A spectrophotometric sensor, comprising:
   a generally planar substrate having a first opening;
   a light emitter positioned within the first opening to be optically coupled to a tissue site;
   one or more photodetectors positioned on the substrate outside the first opening;
   a light scattering medium having a second opening substantially aligned with the first opening and being disposed proximate to the substrate, wherein the light scattering medium is configured to contact the tissue site and increase the effective detection area of the one or more photodetectors; and a light barrier configured to surround the light emitter such that light does not propagate directly from the light emitter to the one or more photodetectors.

2. The spectrophotometric sensor, as set forth by claim 1, wherein the light scattering medium comprises an adhesive.

3. The spectrophotometric sensor, as set forth by claim 2, wherein the adhesive comprises a water-based gel adhesive.

4. The spectrophotometric sensor, as set forth by claim 1, further comprising a light pipe disposed within the light barrier.

5. The spectrophotometric sensor, as set forth by claim 4, wherein the light pipe is comprised of a light transmissive composition.

6. The spectrophotometric sensor, as set forth by claim 1, wherein the substrate comprises one or more openings in which the one or more photodetectors are positioned.

7. The spectrophotometric sensor, as set forth by claim 1, wherein the light barrier comprises an opaque composition or a reflective composition.

8. The spectrophotometric sensor, as set forth by claim 1, wherein the light scattering medium is generally annularly shaped.

9. The spectrophotometric sensor, as set forth by claim 1, wherein the light barrier is an annularly shaped member disposed in the first and second openings and surrounds the light emitter.

10. The spectrophotometric sensor, as set forth by claim 1, wherein the light barrier has a bottom portion with a width greater than a top portion, the bottom portion being configured to secure the light barrier to the light scattering medium.

11. The spectrophotometric sensor, as set forth by claim 1, wherein the substrate is light transmissive.

12. The spectrophotometric sensor, as set forth by claim 1, wherein the substrate is generally annularly shaped.

13. A spectrophotometric sensor, comprising:
a generally planar substrate having a first opening;
a photodetector positioned within the first opening to be optically coupled to a tissue site;
one or more light emitters positioned on the substrate outside the first opening;
a light scattering medium having a second opening substantially aligned with the first opening and being disposed proximate to the substrate, wherein the light scattering medium is configured to be in contact with the tissue site and to increase the effective emission area of the one or more light emitters; and
a light barrier configured to surround the photodetector such that light does not propagate directly from the one or more light emitters to the photodetector.

14. The spectrophotometric sensor, as set forth by claim 13, wherein the light scattering medium comprises an adhesive.

15. The spectrophotometric sensor, as set forth by claim 14, wherein the adhesive comprises a water-based gel adhesive.

16. The spectrophotometric sensor, as set forth by claim 13, further comprising a light pipe disposed within the light barrier.

17. The spectrophotometric sensor, as set forth by claim 16, wherein the light pipe comprises a light-transmissive composition.

18. The spectrophotometric sensor, as set forth by claim 13, wherein the substrate comprises one or more openings in which the one or more light emitters are positioned.

19. The spectrophotometric sensor, as set forth by claim 13, wherein the light barrier comprises an opaque composition or a reflective composition.

20. The spectrophotometric sensor, as set forth by claim 13, wherein the light scattering medium is generally annularly shaped.

21. The spectrophotometric sensor, as set forth by claim 10, comprising a light-transmissive light pipe disposed within the light barrier.

22. The spectrophotometric sensor, as set forth by claim 21, wherein the light barrier is a generally annularly shaped member disposed in the first and second openings and surrounds the photodetector.

23. The spectrophotometric sensor, as set forth by claim 13, wherein the light barrier has a bottom portion with a width greater than a top portion, the bottom portion being configured to secure the light barrier to the light scattering medium.

24. The spectrophotometric sensor, as set forth by claim 13, wherein the substrate is light transmissive.

25. The spectrophotometric sensor, as set forth by claim 13, wherein the substrate is generally annularly shaped.

26. A spectrophotometric sensor, comprising:
a substrate body having a plurality of openings;
at least one light emitter positioned over at least one opening, wherein the at least one light emitter is optically coupled to a tissue site;
at least one photodetector positioned over at least one other opening and adjacent to the at least one light emitter such that the at least one photodetector is on a same side of the substrate body as the at least one light emitter, wherein the at least one photodetector is optically coupled to a light scattering medium; and
an adhesive member disposed on an opposite side of the substrate body as the at least one photodetector and configured to form a patient contact surface of the spectrophotometric sensor, wherein the adhesive member comprises the light scattering medium, and wherein the light scattering medium is configured to increase at least one of the effective detection area of the at least one photodetector or the effective emission area of the at least one light emitter.

27. The spectrophotometric sensor, as set forth by claim 26, wherein the light scattering medium comprises an adhesive.

28. The spectrophotometric sensor, as set forth by claim 27, wherein the adhesive comprises a water-based gel.

29. The spectrophotometric sensor, as set forth by claim 26, wherein the adhesive member and the substrate body are generally annularly shaped.

30. The spectrophotometric sensor, as set forth by claim 26, wherein the substrate body is light transmissive.

31. The spectrophotometric sensor, as set forth by claim 26, comprising a cylindrically shaped light barrier having a hollow interior, wherein the light barrier is configured to reduce or eliminate shunting between the at least one light emitter and the at least one photodetector.

* * * * *